United States Patent [19]

Wakazawa et al.

[11] Patent Number: 4,472,576
[45] Date of Patent: Sep. 18, 1984

[54] PROCESSES FOR THE PRODUCTION OF ANTIBIOTIC 1-OXADETHIACEPHALOSPORINS

[75] Inventors: Tadashi Wakazawa; Taro Niida, both of Yokohama; Shunzo Fukatsu, Ichigayata; Yasushi Murai, Yokosuka; Tsuneo Okonogi, Yokohama; Seiji Shibahara, Machida, all of Japan

[73] Assignee: Merck & Co., Inc., Rahway, N.J.

[21] Appl. No.: 446,534

[22] Filed: Dec. 3, 1982

[51] Int. Cl.$^3$ ............................................. C07D 498/04
[52] U.S. Cl. ...................................... 544/92; 260/141
[58] Field of Search .......................................... 544/92

[56] References Cited

U.S. PATENT DOCUMENTS 4,138,486  2/1979  Narisada et al. ............... 424/248.52
4,174,316  11/1979 Christensen et al. ........... 260/239 A
4,226,866  10/1980 Christensen et al. ........... 424/248.51

OTHER PUBLICATIONS

Malcolm M. Campbell and Graham Johnson, "Formation of Enantiomeric 4-Oxa-2,6-diazabicyclo (3.2.0) hept-2-en-7-ones+from Methyl 6 and 6-Phenoxyacetamidopenicillanates", J.C.S. Perkin I, 1975, pp. 1932-1934.

Primary Examiner—Richard Raymond
Attorney, Agent, or Firm—Thomas E. Arther; Raymond M. Speer; Hesna J. Pfeiffer

[57] ABSTRACT

Disclosed is a process for preparing antibiotic 1-oxadethiacephalosporins via diazo-species I:

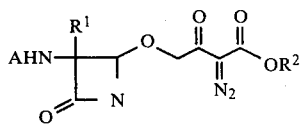

wherein: A is acyl; $R^1$ is H or $OCH_3$; and $R^2$ is a protecting group.

6 Claims, No Drawings

PROCESSES FOR THE PRODUCTION OF ANTIBIOTIC 1-OXADETHIACEPHALOSPORINS

DETAILED DESCRIPTION OF THE INVENTION

This invention relates to a process for preparing 1-oxadethiacephalosporins (I) and their pharmaceutically acceptable salts and esters which are useful as antibiotics via ring-closure of 4-(3'-carboxy-3'-diazo-2'-oxa-propyloxy)-3-acylaminoazetidin-2-ones II:

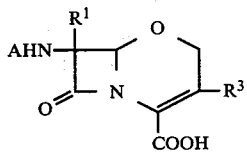

wherein: $R^1$ is H or $OCH_3$; A is H or acyl; and $R^3$ is an organic functional group known in the relevant art as (in this connection see U.S. Pat. Nos. 4,226,866, issued Oct. 7, 1980, and 4,138,486 issued Feb. 6, 1979, respectively. which are incorporated herein by reference to the extent that they define I and its utility);

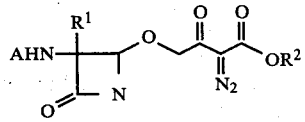

wherein A and $R^1$ are as defined above; and $R^2$ is a removable protecting group.

Compounds containing the oxacephalosporin nucleus of the formula

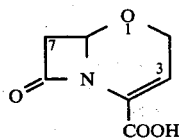

are known as antibiotics having a broad range of antibacterial activity, and there have been reported various methods of synthesizing the oxacephalosporin nucleus. However, all of these prior schemes are multi-step and inefficient.

We, the present inventors, have made extensive researches in an attempt to provide a process of forming the oxacephalosporin nucleus which is free from the drawbacks of the prior art methods. As a result, we have succeeded to synthetize a new compound, carboxyl-protected 4-(3'-carboxy-3'-diazo-2'-oxapropyloxy)-3-acylamino-azetidine-2-one represented by the formula (II)

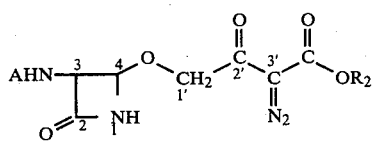

wherein A is an acyl group such as alkanoyl group or aroyl group and $R^2$ is a carboxyl-protecting group, and we have discovered that when the compound of the formula (II) is reacted with such a substance (hereinafter referred to as a carbene-producing catalyst) which is capable of converting into carbene the 3'-carbon atom present in the side-chain attaching to the 4-position of the compound (II), this compound undergoes the ring-closure in such a way that the diazo group ($=N^2$) existing in the compound (II) is liberated, the 3'-carbon atoms is converted into the carbene and then bonded to the nitrogen atom at the 1-position of the azetidinone nucleus of the compound (II). On the basis of these findings, this invention is achieved. As previously mentioned the definition of the acyl group A is incorporated by reference from the above-cited U.S. Patents. Additionally, A is defined to be all acyl functional groups known to be effective in the related $\beta$-lactam antibiotic art which are characterized by an N-acyl moiety.

Also incorporated by reference is U.S. Pat. No. 4,174,316, issued Nov. 13, 1979, which describes the synthesis of "homothienamycin" (I') from the carbon analogue (II') of the above-described diazo intermediate (II):

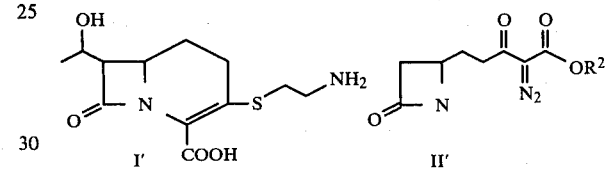

while homothienamycin may be considered a 1-carbadethiacephalosporin, the cited patent makes no disclosure relative to the instant 7-amido-1-oxadethiacephalosporins, or their synthesis. The definition of $R^2$ in the cited patent is specifically incorporated herein.

In accordance with the process of this invention, the ring-closing reaction of the azetidinone derivative of the formula (II) is effected by treating with the carbene-producing catalyst, and hence the new process of this invention is to form the oxacephalosporin nucleus by conducting the ring-enlargement of the azetidinone compound in such a way that the ring-closure takes place at the 4-5 bond of the oxacephalosporin nucleus. The process of this invention is unique in that the formation of the oxacephalosporin nucleus is performed by utilizing only the carbon atoms of the $\beta$-lactam ring of the penicillin molecule which are essentially required to impart the necessary sterochemistry and the necessary antibacterial activity to the cephem ring, but without utilizing the other carbon atoms of the penicillin molecule than those of the lactam ring; and by utilizing an additional compound to introduce externally the further carbon atoms which are required additionally to form the cephem ring, and also in that the ring-closure is effected with involving the carbene-producing reaction. There has never been any precedent where the carbon-producing reaction is involved in the synthetic formation of the oxacephalosporin nucleus.

According to the first aspect of this invention, there is provided a process for the production of a 1-oxa-1-dethia-3-hydroxycephalosporin derivative of the formula

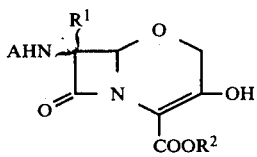

wherein A denotes an acyl group, $R^1$ denotes a hydrogen or a methoxy group and $R^2$ denotes a carboxyl-protecting group, characterized in that a diazo compound represented by the general formula

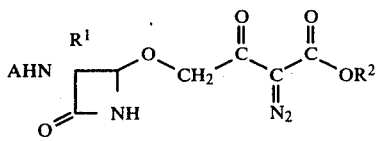

wherein A, $R^1$ and $R^2$ are as defined above is ring-closed by reacting it with a carbene-producing catalyst. According to the second aspect of this invention, there is provided a process for the production of a 1-oxa-1-dethia-3-alkoxycephem compound of the general formula

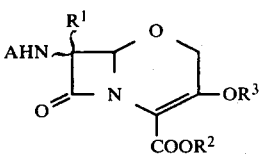

wherein A denotes an acyl group, $R^1$ denotes a hydrogen or a methoxy group, $R^2$ denotes a carboxyl-protecting group and $R^3$ denotes a lower alkyl group, characterized in that a diazo compound represented by the general formula

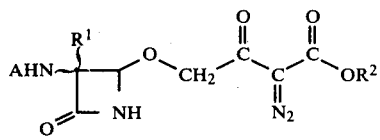

wherein A, $R^1$ and $R^2$ are as defined about is ring-closed by reacting it with a carbene-producing catalyst to produce the 1-oxa-1-dethia-3-hydroxycephalosporin derivative of the formula

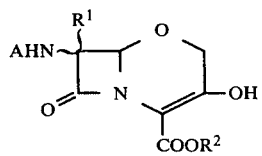

wherein A, $R^1$ and $R^2$ are as defined above, and the 3-hydroxyl group of said derivative of the formula (III) is reacted with an alkylation reagent According to the third aspect of this invention, there is provided the compound of the general formula (II) shown hereinbefore, as the compound of the formula (II) is used as the starting compound in the processes of this invention and is a useful, new substance.

Procedures for carrying out the processes of this invention are now described.

In the diazo compound of the formula (II) which is employed as the starting compound in the processes of this invention, the acyl group (A) may be an alkanoyl group of the formula $R^4CO—$ where $R^4$ is an alkyl group, particularly an alkyl group of 1 to 4 carbon atoms; or an aroyl group of the formula $R^5CO—$ where $R^5$ is an aryl group, particularly phenyl group, optionally bearing an inert substituent such as nitro group which does not participate in the reaction; or an aralkyl-carbonyl group of the formula $R^6CO—$ where $R^6$ is an aralkyl group such as a phenyl-lower-alkyl group, especially benzyl group; or a phenoxy-loweralkyl-carbonyl group, especially phenoxyacetyl group. Preferred examples of the acyl group (A) include benzoyl group, phenylacetyl group and phenoxyacetyl group.

The group $R^1$ may be a hydrogen atom or a methoxy group. This methoxy group may preferably be in $\alpha$-position.

The carboxyl group which is attaching to the 3'-carbon atom of the diazo compound of the formula (II) needs to have been protected. For this protection, there may be selected a suitable one from any known carboxyl-protecting group. Examples of the carboxyl-protecting group ($R^2$) suitable for that purpose include an alkyl group such as t-butyl, dichloroethyl and the like; as well as an aralkyl group such as benzyl, p-nitrobenzyl, p-methoxybenzyl, phenacyl, diphenylmethyl and the like. It is preferable to select a carboxyl-protecting group which can readily be removed either under weakly acidic conditions or under reduction conditions. For instance, it is convenient to select a substituted or unsubstituted aralkyl group such as diphenylmethyl or p-nitrophenylmethyl.

In the processes according to the first and second aspects of this invention, the ring-closing reaction of the diazo compound of the formula (II) is performed using a carbene-producing catalyst. This catalyst may be, for example, rhodium acetate, rhodium oxide or silver oxide etc. Rhodium acetate is most preferred. This ring-closure reaction may be conducted in such a manner that the starting compound (II) is dissolved in an organic solvent such as ethyl acetate, THF, dioxane and the like and the carbene-producing catalyst is reacted with the compound (II) in the solution obtained. The reaction may be conducted preferably at a temperature of 0° C. to 100° C. and more especially at a temperature of 30° C. to 70° C. for a period of 30 minutes to 1 hour.

By the ring-closure reaction stated above, there is produced the 1-oxa-1-dethia-3-hydroxycephalosporin derivative of the general formula (III). This derivative is somewhat unstable and is hard to be isolated as such.

The compound of the general formula (III) thus obtained is, without isolation thereof, alkylated in the process of the second aspect of this invention, whereby the 3-hydroxyl group of the compound (III) is converted into the alkoxyl group. To this end, a diazoalkane may usually be used as the alkylation reagent. The methylation reagent may be diazomethane and the ethylation reagent may be diazoethane, for example. This alkylation reagent may be reacted with the compound (III) in an organic solvent as mentioned above in a known manner. The reaction temperature may be in a range of 0° C. to 50° C.

In this way, the compound of the formula (I) is produced. If desired, the protected 4-carboxyl group ($—COOR^2$) of the compound of the formula (I) may be subjected to a conventional deprotection method, for example, by weak acid hydrolysis, so that the protecting group ($R^2$) is removed therefrom.

The compound of the general formula (I) thus obtained may be purified according to a conventional method for purifying the β-lactam compounds.

When the compound of the general formula (I) obtained by the second aspect of this invention contains α-methoxy group as the group $R^1$, the acylamino group (AHN—) is then existing in the α-position.

On the other hand, when the compound (I) contains hydrogen atom as $R^1$, the aminoacyl group (AHN—) may be existing either in the α-position or in the β-position. The compound (I) containing a β-acylamino group as the group AHN— may be subjected to an acyl-exchange reaction in a known manner, so that there is derived a useful substance having antibacterial activity, for example, such antibacterial substances as disclosed in Japanese patent application prepublication "Kokai" No. 112895/78. The compound (I) containing an β-acylamino group as the group AHN— may be modified into antibacterial substances by transferring the α-acylamino group into the β-position in a known manner with concurrent α-methoxylation at the 7-position of the compound (I), followed by exchanging the resultant β-acylamino group by another appropriate acylamino group.

A method for preparing the diazo compound of the general formula (II) which is employed as the starting compound in the processes of this invention is now described.

As demonstrated in Example 2 given later, the compound of the formula (II) can be prepared via a few stages with starting from the compound of the general formula

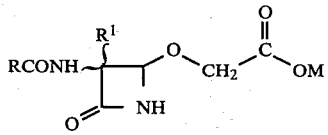

wherein R is phenyl group, phenylmethyl group or phenoxymethyl group, $R^1$ is hydrogen or methoxy group and M is an alkali metal, which is, in turn, synthetized by several stages using an oxazoline derivative and glycerine or hydroxyacetic acid alkylester as the inital materials. If the nature of the 3-acylamino group (RCONH—) present in the compound (IV) is not consistent with the nature of the corresponding acylamino group (AHN—) present in the starting diazo compound (II) to be employed in the processes of this invention, the compound (IV) may be subjected to an acyl-exchange reaction in a known manner so as to introduce an appropriate acylamino group AHN— thereinto and to give the compound of the formula

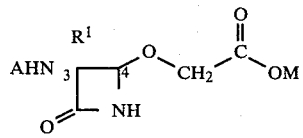

Subsequently, the compound of the formula (IV') is converted into a corresponding free acid form by neutralization, followed by activation of the terminal carboxyl group of the side-chain which is attaching to the 4-position of the compound (IV'). The activated carboxylic acid derivative so obtained of the compound (IV') is then reacted with two carbon atoms unit in such a manner that it is reacted with an alkali metal or alkaline earth metal salt of malonic acid mono-ester or acetate anion and the like, for example, whereby there is produced a compound represented by the general formula

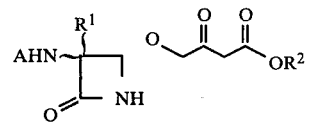

wherein A and $R^1$ are as defined above and $R^2$ is a carboxyl-protecting group. Further, the compound (V) is reacted with an azide compound to give a diazo compound represented by the general formula

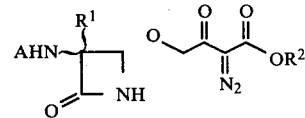

wherein A, $R^1$ and $R^2$ are as defined above.

In the above-mentioned stages for the preparation of the starting compound, the reaction stages of preparing the compound (V) from the compound (IV) may be conducted by so-called "one-pot" system, in such a way that the compound (IV') in solution in an organic solvent such as acetonitrile, THF and the like is firstly converted into the free acid form by neutralization with a mineral acid such as hydrochloric acid and sulfuric acid etc. and the terminal carboxyl group of the side-chain at the 4-position of the compound (IV') but in the free acid form is then converted into the activated carboxylic acid derivative. For the activation of the terminal carboxyl group, there may be applied any known procedure such as the mixed acid anhydride method, the acid halide method, the active imidazolide method and the like. When the activation of the terminal carboxyl group is conducted using carbonyl diimidazole, for example, the free acid form of the compound (IV') may be reacted with carbonyl diimidazole at a temperature of 0° C. to 5° C. for a period of 1 to 2 hours. The carboxyl-activated form of the compound (IV') so obtained is then subjected to the two-carbon-atoms-extension reaction in solution in the organic solvent mentioned above to produce the compound of the formula (V). For the two-carbon-atoms-extension reaction to produce the compound (V), there is used a two-carbon-atoms-extension reagent such as the anion of malonic acid mono-ester, acetate anion, Meldrum's acid derivative anion and the like. This reaction may preferably be carried out at a temperature of 5° to 20° C. for a period of 3 to 4 hours.

In the subsequent stage where the compound of the general formula (V) is converted into the diazo compound of the general formula (VI), this dizaotization reaction may be conducted using an azide compound. To this end, the azide compound may suitably be an aromatic sulfonic acid azide of the formula

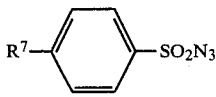

wherein R[7] is a hydrogen, carboxyl group or an alkyl group of 1 to 9 carbon atoms. A most preferred one is the azide of the formula (VII) where R[7] is carboxyl group. This diazotization is carried out in such a manner that the compound of the general formula (V) is dissolved in an organic solvent such as acetonitrile, dioxane, THF and the like, the resultant solution is admixed with the diazotization reagent of the formula (VII) and the reaction is effected at a temperature of 0° C. to 30° C. under stirring, followed by dropwise addition of an organic base such as triethylamine, dimethylaniline and the like to complete the reaction.

The processes of this invention are now illustrated with reference to the following Examples, to which this invention is not limited. Procedures for preparation of the starting diazo compound (II) employed in the present processes are illustrated by Example 2.

EXAMPLE 1

Synthesis of (6R,7R)-7-benzoylamino-3-methoxy-1-oxa-1-dethia-4-p-nitrophenylmethoxycarbonyl-3-cephem (a) The diazo compound of the formula

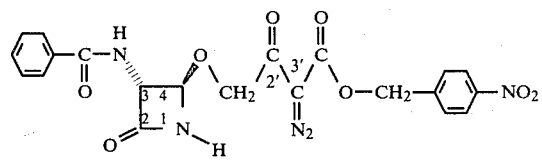

that is, (3R,4R)-4-(3'-p-nitrophenylmethoxycarbonyl-3'-diazo-2'-oxapropyloxy-3-benzoylamino-azetidin-2-on (30 mg; 0.064 m mol) (see Example 2 given later) and rhodium acetate (Rh(OAc)$_2$(0.4 mg) were suspended in 6 ml of ethyl acetate, and through the resulting suspension was passed gaseous nitrogen for 20 minutes, followed by heating at 45°–48° C. During this heating, the starting compound employed was slowly dissolved in the ethyl acetate to give a solution. The resultant solution was allowed to stand at 45°–48° for 30 minutes to effect the reaction, affording the reaction solution containing therein the compound of the formula

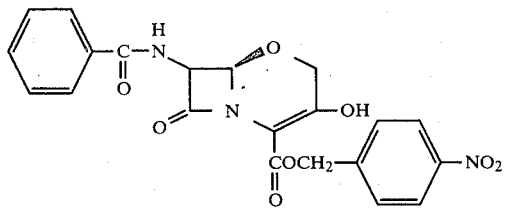

which was formed by the ring-closure reaction involved.

(b) The reaction solution was obtained as above was ice-cooled and then admixed with 6 ml of a solution containing 0.1 m mol/ml of diazomethane in ethylether. The admixture was subjected to the reaction for 5 minutes under ice-cooling and then at ambient temperature for 15 minutes to effect the methylation of the 3-hydroxyl group.

The resultant reaction solution was filtered to remove the solid matter, and the filtrate was distilled to remove the organic solvent therefrom. The yellow colored solid (33 mg) obtained was taken up into chloroform and chromatographed on 660 mg of silica gel (Wako Gel) by developing with 10 ml of chloroform. The silica gel column was then eluted with chloroform-ethyl acetate (10:1 by volume) and the eluate was distilled to remove the solvent therefrom. A crystalline product (17 mg) was afforded. Yield 58%, m.p. 192°–193° C. This crystalline product gave an Rf 0.33 when it was subjected to a thin layer chromatography on silica gel developed with benzene-ethyl acetate (1:1 by volume).

NMR (CDCl$_3$): 3.8 (s. 3H); 4.5 (ABq.2H); 4.9 (dd J=8.1 1H); 5.05 (d. J=1 1H); 5.35 (ABq 2H); 6.85 (d J=8 1H); 7.3–8.2 (9H).

Mass spectrometry: 439 (M+).

IR. spectrum (Nujol): 1790, 1705, 1640 cm$^{-1}$.

This product was identified to be the titled compound of the formula

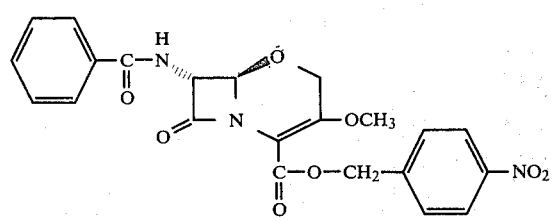

EXAMPLE 2

Synthesis of (3R,4R)-4-(3'-p-nitrophenylmethoxy-carbonyl-3'-diazo-2'-oxapropyloxy-3-benzoylamino-azetidin-2-on (a) Production of (3R,4R)-4-(sodiocarboxymethoxy)-3-benzoylamino-azetidin-2on (i) The oxazoline derivative of the formula

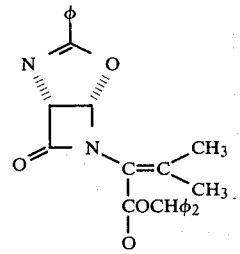

wherein O denotes phenyl group, that is, 3-benzhydryl-methyl-2[1R,5S)-3-phenyl-7-oxo-4-oxa-2,6-d iazabicyclo[3,2,0]hept-2-en-6-yl] but-2-enoate (4.52 g; 10 m mol) (disclosed in a chemical literature "J. Chem. Soc. Perkin I" 1975, p. 1932) was dissolved in 500 ml of ethyl acetate, and the resulting solution was admixed with 8.3 g (90 m mol) of glycerine of the formula

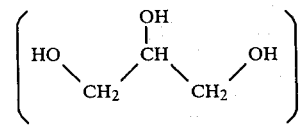

followed by agitation under ice-cooling. To the admixture was further added 0.4 ml of boron trifluoride-ethylether complex (BF₃.Et₂O), 0°–5° C. for 30 minutes. After admixture was subjected to the reaction at 26-2 for 2.5 hours and then admixed with 25 ml of an aqueous sodium hydrogen carbonate under ice-cooling. The reaction solution obtained was allowed to stand so that the organic phase was separated from the aqueous phase. The organic phase was removed, washed with two 50 ml-portions of 50% aqueous sodium chloride and then with one 50 ml-portion of water and dried, followed by removal of the organic solvent by distillation to yield 5.26 g of a foamed solid.

This solid comprises the compound represented by the formula

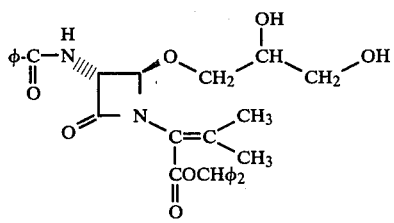

(ii) The foamed solid (5.26 g) obtained as above was dissolved in 200 ml of tetrahydrofuran (THF), and to the resultant solution was added dropwise under ice-cooling a solution which was prepared by dissolving 2.44 g (11.5 m mol) of sodium periodate (NaIO₄) in 114 ml of 1N sulfuric acid. The admixture obtained was stirred at 0°–5° C. for 20 minutes for the reaction, followed by further reaction at ambient temperature for 3 hours. The reaction solution was ice-cooled and then poured into a mixture of 1 l of ethyl acetate and 600 ml of water, and the whole mixture was allowed to stand so as to separate the organic phase from the aqueous phase. The aqueous phase was re-extracted with 100 ml of ethyl acetate, and the ethyl acetate extracts were combined with the aforesaid organic phase. The combined organic phase was washed with 100 ml of a saturated solution of sodium hydrogen carbonate in water and then with three 200 ml-portions of water, followed by drying and distillation to remove the organic solvent therefrom. A solid was afforded. Yield 4.92 g.

This solid was taken up in a volume of benzene and passed through a column of 98 g of silica gel (Wako Gel). The silica gel column was eluted with benzene-ethyl acetate (3:1) and the eluate was distilled to remove the organic solvent, affording 2.2 g of an aldehyde compound of the formula

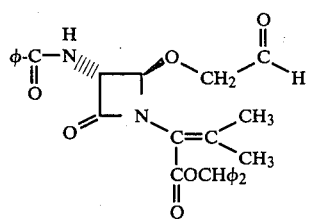

Yield 40.4%. This aldehyde compound gave an Rf 0.33 when it was subjected to a thin layer chromatography on silica gel developed with benzene-ethyl acetate (1:1).

NMR (CDCl₃): 2.0 (s.3H); 2.25 (s.3H); 4.25 (s.2H); 4.8 (d.J=8.1H); 5.1 (s.1H); 6.85 (s.1H); 7.0–7.7 (15H); 9.5 (s.1H).

Mass spectrometry (m/e): 512 (M+).

Further, the above-mentioned silica gel column was eluted with benzene-ethyl acetate (1:1) and the eluate was distilled to remove the organic solvent, when there was recovered 360 mg (Yield 6.5%) of the compound of the formula

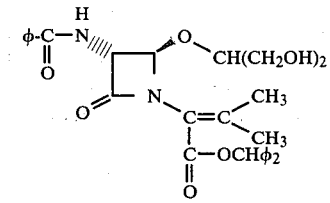

which was by-produced through the reaction of the compound (b) with the glycerine as a secondary alcohol.

(iii) The aldehyde compound (3.74 g; 7.23 m mol) of the formula (c) obtained in the above stage (ii) was dissolved in 37 ml of acetone, and to the resultant solution was dropwise added slowly (over about 10 minutes) 2.4 ml of a solution of 0.7 m mol/ml of chromium trioxide (CrO₃) in sulfuric acid (H₂SO₄) at 0° C. to 5° C. under ice-cooling. After reaction for 15 minutes, the reaction solution was subjected to further reaction at ambient temperature for 15 minutes. The reaction solution was then admixed with 0.96 ml of methanol, agitated for 10 minutes and then admixed with 280 ml of ethyl acetate and 140 ml of a saturated aqueous solution of sodium chloride. The admixture obtained was allowed to stand so as to separate the organic phase from the aqueous phase. The organic phase was removed, washed with two 70 ml-portions of an aqueous solution of 50% saturation of sodium chloride and then with two 70 ml-portions of water, followed by drying over anhydrous magnesium sulfate and distillation to remove the organic phase therefrom. A crystalline product was afforded in a yield of 3.44 g. This product was slurried with addition of about 50 ml of ethylether for the washing purpose, followed by evaporation of the ethylether to yield 3.0 g of crystals. m.p. 167–167 5° C. Yield 79%. This product gave an Rf 0.33 when it was subjected to a thin layer chromatography on silica gel developed with water-saturated ethyl acetate-methanol (3:1). The product was the hydroxyacetic acid derivative represented by the formula

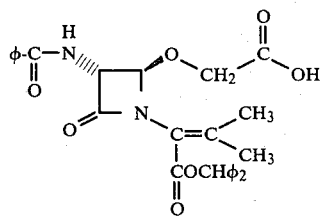

NMR (CDCl₃): δ2.0 (s.2H); 2.2 (s.2H); 4.1 (ABq.2H); 4.75 (d.J=8.1H); 5.1 (s.1H); 6.8 (s.1H); 7.0–7.7 (15H).

Mass spectrometry (m/e): 528 (M+).

IR. spectrum (Nujol): 1765, 1720, 1635 cm⁻¹.

(iv) The hydroxyacetic acid derivative (1.7 g) of the formula (e) obtained in the above stage (iii) was dissolved in 55 ml of methanol, and into the resultant solution was passed gaseous ozone (O₃) with cooling to a temperature of −55° C. to 50° C. The reaction was completed in 45 minutes. Thereafter, a stream of air was passed through the reaction solution to remove the ozone therefrom, and to the reaction solution was added slowly 160 ml of ethyl acetate. The admixture obtained was poured into 320 ml of a solution of 17 g of sodium hydrogen sulfite (NaHSO₃) in water, and the whole mixture was allowed to stand so as to separate the organic phase from the aqueous phase. The organic phase was removed, washed with three 30 ml-portions of water and dried over anhydrous magnesium sulfate, followed by distillation of the organic solvent to afford 1.7 g of an oily product. This product was the compound of the formula

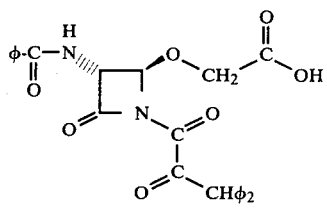

(v) The oily product (1.7 g) of the formula (f) obtained in the above stage (iv) was dissolved in 17 ml of acetone, and the solution in acetone was added dropwise to a mixtue (at pH 10) of 290 ml of methanol and 5.8 ml of water containing 270 mg (3.22 m mol) of sodium hydrogen carbonate dissolved therein. After this, the admixture obtained was raised to ambient temperature, followed by reaction for 30 minutes, when the reaction solution was discolored into pale yellow color from the yellow color of the solution which was observed just after the dropwise addition of the compound of the formula (f). The reaction solution was distilled to remove the organic solvent, and the residue was dried in vacuo for 2 hours and then solidified by addition of 50 ml of ethylether. The material so solidified was filtered and dried over phosphorus penta-oxide to give 880 mg of a solid. m.p. 155° C. (dec.). Yield 95%. This product gave and Rf 0.2 when it was subjected to a thin layer chromatography on silica gel developed with water-saturated ethyl acetate-methanol (3:1). This product was in the form of the sodium salt of the compound represented by the formula

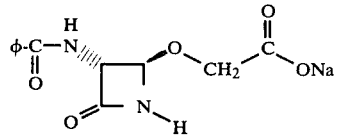

which was the titled compound, (3R,4R)-4-(sodiocarboxymethoxy)-3-benzoylamino-azeridin-2-on. NMR (DMSO-d6): 4.15 (s.2H); 4.65 (d J=8.1H); 5.2 (d J=1 1H); 7.3–7.9 (5H); 8.95 (bs 1H); 9.1 (d J=8 1H).

Mass spectrometry: 3300, 1755, 1740, 1645 cm⁻¹.

(b) Production of (3R,4R)-4-(3′-trophenylmethoxycarbonyl-2′-oxapropyloxy)-3-benzoylamino-azetidin-2-on The sodium salt compound (57 mg; 0.2 m mol) of the formula (g) obtained in the above stage (a) (v) was suspended in THF, and to the resulting suspension was added dropwise 63 μl of an anhydrous solution of 3N hydrogen chloride in dioxane (equivalent to 0.19 m mol of HCl) under ice-cooling. After the reaction was effected for 15 minutes under ice-cooling, the reaction solution was distilled to remove the solvents. The resideue was dried well under reduced pressure to give 66 mg of a solid. This solid was dissolved in 3 ml of acetonitrile and the resulting solution was admixed with 36 mg (0.22 m mol) of carbonyldiimidazole

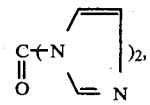

and the reaction was conducted for 4 hours under stirring and ice-cooling. The reaction solution obtained contained the active amide (imidazolide of the formula

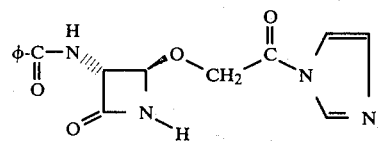

produced.

To the above-mentioned reaction solution was added 120 mg (0.24 m mol) of the magnesium salt of malonic acid mono-(p-nitrophenylmethyl)ester represented by the formula

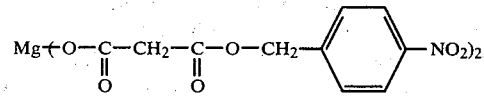

and the resultant mixture was agitated for 30 minutes under ice-cooling and then for 2.5 hours at ambient temperature to effect the reaction. By the two-carbon-atoms-extension reaction involved, there was produced in the reaction solution the titled compound of the formula

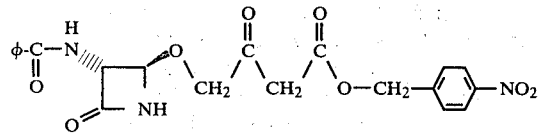

This reaction solution containing the titled compound as above was again ice-cooled and admixed with 5 ml of ethyl acetate, followed by dropwise addition of 4 ml of an aqueous solution of 0.5N HCl thereto (pH ca. 2). The resultant admixture was allowed to stand so as to separate the organic phase from the aqueous phase. The organic phase was removed, washed with 5 ml of water and then with 10 ml of an aqueous solution of 50% saturation of sodium hydrogen carbonate and subsequently dried over anhydrous magnesium sulfate. Concentration of the dried organic phase gave 80 mg of a yellow-colored oily product.

This yellow-colored oily product was taken up into ethyl acetate and the resulting solution was passed through a column of 1.4 g of silica gel (Wako Gel), followed by development of the silica gel column with 20 ml of chloroform. This column was then eluted with chloroform-ethyl acetate (1:1), and from the eluate was isolated 42 mg of the titled compound of the formula (j) in the form of the β-keto-ester. m.p. 151°–153° C. Yield 47%.

NMR (CD$_3$COCD$_3$): δ3.8 (s.2H); 4.55 (s.2H); 4.85 (dd J=8 J=1 1H); 5.35 (3H); 7.4–8.5 (10H).

Mass spectrometry (m/e): 441 (M$^{30}$).

IR. spectrum (Nujol): 3350, 1775, 1740, 1720, 1640 cm$^{-1}$.

(c) Production of (3R,4R)-4-(3'-p-nitrophenylmethoxycarbonyl-3'-diazo-2'-oxapropyloxy)-3-benzoylaminoazetidin-2-on The β-keto-ester compound (67 mg; 0.15 m mol) of the formula (j) obtained in the above stage (b) was dissolved in acetonitrile (6 ml), and the resultant soluton was ice-cooled and then admixed with 42 mg (0 18 m mol) of p-carboxybenzene-sulfonic azide under stirring. Ten minutes later, to the reaction solution was added dropwise 77 μl (0.52 m mol) of triethylamine, followed by effecting the reaction for 10 minutes under ice-cooling and then at ambient temperature. After the reaction continued for 50 minutes, the precipitated deposited was removed from the reaction solution by filtration and the filtrate was concentrated. The solid residue obtained was taken up into a mixture of benzene-ethyl acetate (1:1) and the resultant solution was passed through a column of 1.6 g of silica gel (Wako Gel), followed by development of the column with 20 ml of benzene-ethyl acetate (1:1). The silica gel column was then eluted with ethyl acetate and the eluate was distilled to remove the solvent. The titled diazo compound of the formula

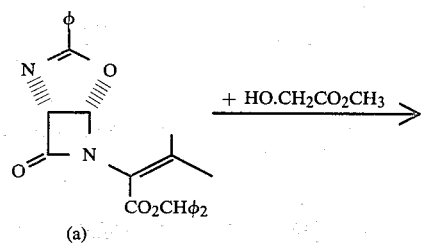

was afforded in a yield of 61 mg m.p. 167° C. (dec.). Yield 87%. This compound gave an Rf 0.22 when it was subjected to a thin layer chromatography on silica gel developed with benzene-ethyl acetate (1:1).

NMR (CD$_3$COCD$_3$): δ4.75 (dd J=8 J=1 1H); 4.8 (s.2H); 5.25 (dJ=1 1H); 5.4 (s.2H); 7.4–8.5 (10H).

IR spectrum (Nujol): 3300, 2170, 1780, 1773, 1720 cm$^{-1}$.

EXAMPLE 3

This example illustrates another route for the preparation of the hydroxyacetic acid derivative of the formula (e) shown hereinbefore, with starting from the oxazoline derivative of the formula (a) employed in the stage (a) (i) of the preceding Example 2 and by reacting said oxazoline derivative with hydroxyacetic acid methylester.

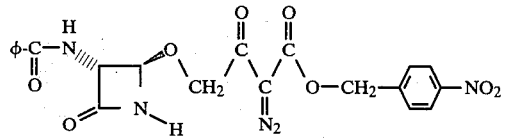

+ HO.CH$_2$CO$_2$CH$_3$ →

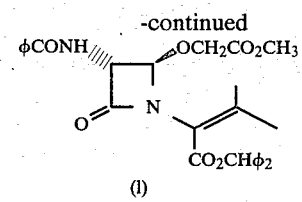

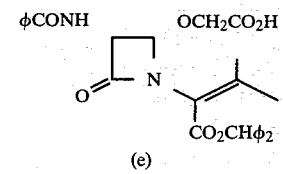

where Ο denotes phenyl group.

The oxazoline derivative of the above formula (a) (5 g; 1.1 m mol) was dissolved in 500 ml of ethyl acetate and the solution obtained was admixed with 40 ml of hydroxyacetic acid methylester, followed by ice-cooling and stirring. To the cold solution obtained was added 0.4 ml of boron trifluoride-ethylether complex (BF$_3$.Et$_2$O) at 0° C. to 5° C. The reaction was effected at 0°–5° C. for 30 minutes and then at ambient temperature for 2 hours. The resulting reaction solution was admixed with 2.5 ml of aqueous sodium hydrogen carbonate and 100 ml of aqueous 50% sodium chloride, and the admixture was agitated violently and then allowed to stand so that the organic phase was separated from the aqueous phase. The organic phase was removed, washed with 100 ml of water and then dried over anhydrous sodium sulfate. The dried organic phase was concentrated to dryness to give 5.9 g of the intermediate product of the above formula (1).

This crude, intermediate product was dissolved in 200 ml of acetone and then the solution was admixed with 9.9 ml of an aqueous solution of 1N sodium carbonate. The reaction was effected for 1 hour and the reaction solution was admixed with 9.9 ml of an aqueous solution of 1N hydrogen chloride, followed by concentration to dryness to give 6.2 g of the solid residue. This residue was washed with water and dried to yield 5.4 g of the compound of the formula (e).

What is claimed is:

1. A process for the production of a 1-oxa-1-dethia-3-hydroxycephalosporin derivative of the formula

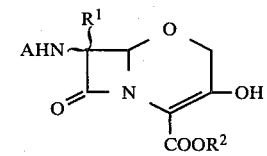

wherein A denotes an acyl group, R$^1$ denotes a hydrogen or a methoxy group and R$^2$ denotes a carboxyl-protecting group; comprising ring-closing:

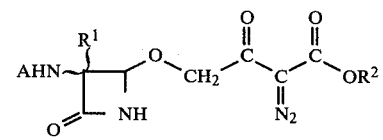

in the presence of a carbene-producing catalyst.

2. A process for the production of a 1-oxa-1-dethia-3-alkoxycephem compound of the general formula

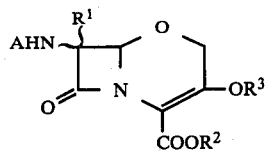

wherein A denotes an acyl group, R¹ denotes a hydrogen or a methoxy group, R² denotes a carboxyl-protecting group and R³ denotes a lower alkyl group; comprising treating:

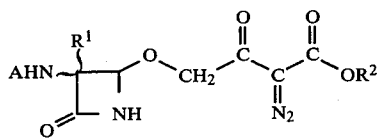

wherein A, R¹ and R² are as defined above with a carbene-producing catalyst to produce the 1-oxa-1-dethia-3-hydroxy-cephalosporin derivative of the formula

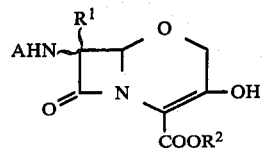

wherein A, R¹ and R² are as defined above; followed by treating with an alkylation reagent calculated to establish R³.

3. A process according to claims 1 or 2 wherein A is an alkanoyl group of the formula R⁴CO— where R⁴ is an alkyl group; or an aroyl group of the formula R⁵CO— where R⁵ is an aryl group; or an acyl group of the formula R⁶CO— wherein R⁶ is an aralkyl group; or a phenoxy-loweralkyl-carbonyl group.

4. A process according to claim 3, wherein A is benzoyl, phenylacetyl, or phenoxyacetyl.

5. A process according to claims 1 or 2 wherein the carbene-producing catalyst is selected from the group consisting of: rhodium acetate, rhodium oxide and silver oxide.

6. The process according to claim 1 wherein A is R—CO— wherein R is selected from: alkyl having 1–6 carbon atoms, phenyl, p-nitrophenyl, p-methoxyphenyl, 2-thienyl, 3-thienyl, benzyl, phenoxymethyl, or thienylmethyl; and R² is selected from: t-butyl, dichloroethyl, trichloroethyl, benzyl, p-nitrobenzyl, p-methoxybenzyl, phenacyl, diphenylmethyl.

* * * * *

UNITED STATES PATENT AND TRADEMARK OFFICE
CERTIFICATE OF CORRECTION

PATENT NO. : 4,472,576
DATED : Sept. 18, 1984
INVENTOR(S) : TADASHI WAKAZAWA et al.

It is certified that error appears in the above—identified patent and that said Letters Patent is hereby corrected as shown below:

Title Page - First Column - currently reads:

[73] Assignee: Merck & Co., Inc., Rahway, N. J.

should be corrected to read:

[73] Assignee: Meiji Seika Kaisha, Ltd., Tokyo, Japan

Signed and Sealed this

Nineteenth Day of March 1985

[SEAL]

Attest:

DONALD J. QUIGG

Attesting Officer      Acting Commissioner of Patents and Trademarks